United States Patent [19]

Capraro et al.

[11] Patent Number: 5,358,940
[45] Date of Patent: Oct. 25, 1994

[54] CHELATE COMPLEXES AND PROCESSES FOR THEIR PREPARATION

[75] Inventors: Hans G. Capraro, Rheinfelden; Marcus Baumann, Basel, both of Switzerland

[73] Assignee: Ciba-Geigy Corporation, Ardsley, N.Y.

[21] Appl. No.: 22,246

[22] Filed: Feb. 25, 1993

[30] Foreign Application Priority Data

Feb. 27, 1992 [CH] Switzerland .................... 600/92

[51] Int. Cl.$^5$ .................... A61K 31/40; C07J 73/00
[52] U.S. Cl. .................... 514/63; 540/3; 540/4; 514/176; 514/183
[58] Field of Search ............ 540/3, 4; 514/174, 176, 514/63, 183

[56] References Cited

FOREIGN PATENT DOCUMENTS

| | | |
|---|---|---|
| 451103 | 3/1991 | European Pat. Off. . |
| 0457196 | 11/1991 | European Pat. Off. . |
| 9118006 | 11/1991 | PCT Int'l Appl. . |
| 9201753 | 2/1992 | PCT Int'l Appl. . |
| 9118007 | 11/1991 | World Int. Prop. O. ......... 536/17.4 |

OTHER PUBLICATIONS

Joyner et al. JACS vol. 82, 1960 pp. 5790–5792.
Freedman, et al. J. Org. Chem. 1991 56 670–672.
Joyner et al. Inorganic Chem. 1962, 1, pp. 236–238.
Boksanyi, et al. Helv. Chim. Acta, 59(3), 1976 pp. 717–727.
Davis, J. Chem. Soc. 1962 pp. 178–181.
Pedersen, JACS vol. 89, 1967 pp. 7017–7036.
Borisenkova et al Chemical Abstracts, vol. 91. 1979, Abstract 9929w.
Nevin et al Inorganic Chemistry 1987 26 891–899.
Keppeler et al. Chem. Ber. 119 3363–3381, 1986.
Manivannan et al. Chemical Abstracts, vol. 110, 1989 Abstract 143348v.
Janda et al. Chemical Abstracts, vol. 111, 1989 Abstract 66590j.
Miyazaki et al Chemical Abstracts vol. 111, 1989 Abstract 144225k.
Mooney, et al. JACS 97(11), 1975, pp. 3033–3038.
Wheeler et al JACS vol. 106, 1984 7404–7410.
Rihter, et al. Chem. Abs. vol. 117, 1992 Abstract 187382a.

(List continued on next page.)

*Primary Examiner*—Mukund J. Shah
*Assistant Examiner*—Pavanaram K. Sripada
*Attorney, Agent, or Firm*—Irving M. Fishman; Karen G. Kaiser

[57] ABSTRACT

Naphthalocyanine-chelate complexes of formula I

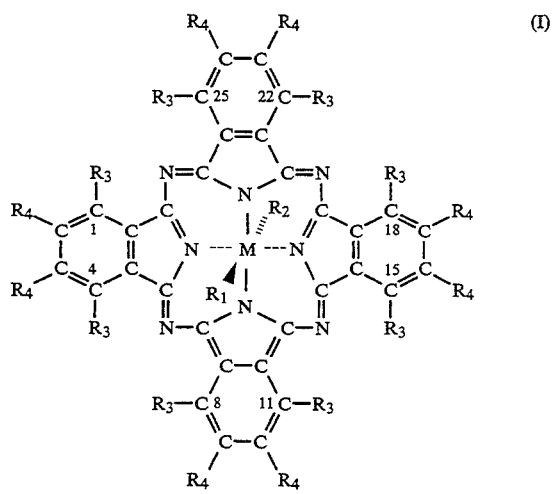

are described which contain as central atom M aluminum, gallium, indium, tin, ruthenium or preferably germanium and in which the remaining symbols are as defined in claim 1. The complexes can be used inter alia in the photodynamic chemotherapy of tumors.

10 Claims, No Drawings

OTHER PUBLICATIONS

Hoh et al., Chemical Abstracts, vol. 111, 1989 Abstract 224443Os.

Shatskaya, et al. Chemical Abstracts vol. 108, 1988 Abstract 57881r.

Rihter et al: "Synthesis and Photoproperties of Diamagnetic Octabutoxyphthalocyanines with Deep Red Optical Absorbance" J. Am. Chem. Soc. BD 112, (1990) pp. 8064–8070.

Cuomo et al: Tumor-Localizing and -Photosensitizing Properties of Liposome-Delivered Germanium (IV) Octabutoxyphthalacyanine—Chemical Abstracts vol. 116, (1992) Columbus Ohio 37092w. p. 351.

Esposito J et al. "Infrared and Nuclear Magnetic Resonance Studies of Some Germanium Phthalocyanines and Hemiporphyrazines" Inorganic Chemistry BD 6, Nr 6, (1967 pp. 1116–1120.

Era et al "Optical Recording Medium with Phthalocyanine Recording Film" Chemical Abstracts vol. 112: (1990) Columbus Ohio 108644h p. 680.

Kobayashi et al "Phthalocyanine Compounds and OPtical Information Recording Media Using Them and Their Manufacture" Chemical Abstract vol. 114–(1991) Columbus Ohio. 111977r p. 672.

Perry et al "Excited State Absorption and Optical Limiting in Solutions of Metallophthalocanines" Chemical Abstracts vol. 115 (1991) Columbus Ohio–243124r p. 750.

Semenov S. G. et al "Quantum Chemical Calculation of the Electronic Absorption Spectra and Ionization Potentials of Silicon and Germanium PHthalocyanine [PcSi(OSiMe$_3$)$_2$] and PcGe(OSiMe$_3$)$_2$] and Silicon Tetrazporphyrin [TAPSI(OSiMe$_3$($_2$]" Chemical Abstracts; vol. 11 (1989)—Columbus Ohio 143681 p. 572.

Cuomo et al, "Tumour-Localising and -Photosensitizing Properties of Liposome-Delivered GE(IV)-Octabutoxyphthalocyanine" Br. J. Cancer 64 (1991) 93–95.

Sounik et al "Synthesis and Characterization of Naphthalocyanines and Phthalocyanines of Use in Sensitizer Studies" SPIE 1203–(1990) 224–229.

Richter et al "Three New Phthalocyanines with Potential for PDT Studies" SPIE 1645 (Jan. 1992) 251–258.

Chemical Abstract 116–121677u (1992) p. 691 Miyazaki "Write-once-type Optical Disk Containing Phtalocyanine Dye" corresponding to JP 03,281,388.

Chemical Abstract 113–142433u (1990) p. 709–710 Sakamoto et al "Optical Recording Medium Containing Phthalocyanine Derivative" corresponding to JP 01,297,293.

Cuomo et al "Liposome-Delivered Si(TV)-Naphthalocyanine as a Photodynamic Sensitiser for Experimental Tumors: Pharmacokinetic and Phototherapeutic Studies" Br. J. Cancer 62 (1990) 966–970.

Derwent Abstract Nr 89-288563/40. Toyo Ink Mfg KK.

CHELATE COMPLEXES AND PROCESSES FOR THEIR PREPARATION

The invention relates to chelate complexes comprising phthalocyanine compounds as complex formers and certain organic derivatives of elements of main groups III and IV of the Periodic Table of Elements having an atomic number of from 31 to 50 inclusive and of aluminium or ruthenium as central atom, to pharmaceutical compositions comprising those complexes, to processes for their preparation and to their use as medicaments, in the purification of blood outside the organism and for diagnostic purposes.

A number of phthalocyanine complexes are already known. In addition, the use of zinc-phthalocyanine in photodynamic chemotherapy for the treatment of tumours has been described (J. D. Spikes, Photochem. Photobiol. 43, 691 (1986)). For example, zinc-phthalocyanine was administered intraperitoneally to mice or rats in the form of an aqueous suspension and a carcinoma produced beforehand in the experimental animals was irradiated with high-energy light, preferably with directed visible light (LASER).

In photodynamic chemotherapy the residence time of the complexes in the organism is of crucial importance because during the treatment the patients are extremely sensitive to light quite generally and must especially avoid exposure to sunlight. For this reason it is also necessary to find compounds that as far as possible concentrate selectively in the tumour and are present in as low a concentration as possible in the healthy parts of the organism. In human therapeutic use the mode of administration also plays a part. Intraperitoneal administration is generally problematic because of the pain caused on penetration of the abdominal cavity and the high degree of skill required of the doctor. There is therefore a need for new complexes that offer advantages over the known complexes from the point of view of mode of administration, selectivity towards tumours and/or residence time in the organism.

The invention relates especially to chelate complexes of formula I

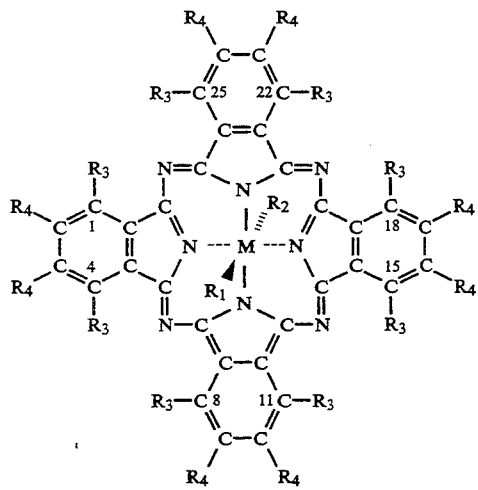

wherein

M is an element of main group III or IV of the Periodic Table having an atomic number of from 31 to 50 inclusive, aluminium or ruthenium, $R_1$ is a radical of formula II

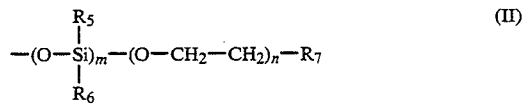

wherein m is 0 or 1, n is an integer from 0 to 200 inclusive, $R_5$ and $R_6$ are each independently of the other lower alkyl or unsubstituted or substituted phenyl, and $R_7$ is alkylthio having up to 20 carbon atoms, alkanoyloxy having up to 20 carbon atoms, 4-(2,3,4,6-tetra-O-acetyl-$\beta$D-D-glucopyranos-1-yloxy)-phenoxy, cholestan-3-yloxy, cholesteryloxy, unsubstituted or cholestan-3-yloxy- or cholesteryloxy-substituted aliphatic hydrocarbyloxy having up to 24 carbon atoms in the aliphatic moiety or, when m is 1 and n is 0, aliphatic hydrocarbyl having from 6 to 24 carbon atoms, or unsubstituted or substituted phenyl, or is a radical of formula III

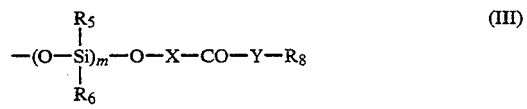

wherein

X is a bivalent aliphatic hydrocarbon radical having up to 23 carbon atoms,

Y is oxygen or the group —NH—, $R_8$ is cholesteryl, aliphatic hydrocarbyl having up to 24 carbon atoms or unsubstituted or cholesteryloxy-substituted aliphatic hydrocarbyl having up to 24 carbon atoms in the aliphatic moiety, and $R_5$, $R_6$ and m are as defined above, $R_2$ has the same definition as $R_1$ when M is an element of main group IV, or $R_2$ is absent when M is an element of main group III or ruthenium, $R_3$ is hydrogen, lower alkyl, lower alkylthio, unsubstituted or lower alkoxy-substituted alkoxy having up to 20 carbon atoms, tri-lower alkylsilyl or halogen, and $R_4$ is hydrogen, lower alkyl, lower alkylthio, unsubstituted or lower alkoxy-substituted alkoxy having up to 20 carbon atoms, tri-lower alkylsilyl or halogen, to novel intermediates for the preparation of those complexes, to pharmaceutical compositions comprising those complexes, to processes for their preparation and to their use as medicaments, for the purification of blood outside the organism and for diagnostic purposes.

An element of main group III and IV of the Periodic Table having an atomic number of from 31 to 50 inclusive is gallium, indium or tin, and preferably germanium.

In a radical of formula II, n is preferably an integer from 0 to 20 inclusive, especially from 0 to 5 inclusive. When n is a number greater than 8 up to and including 200, n may also represent the average values in compound mixtures.

Unsubstituted or substituted phenyl $R_5$ or $R_6$ is preferably unsubstituted phenyl or phenyl substituted by from one to preferably not more than three customary phenyl substituents, for example by lower alkyl, lower alkoxy, halogen, trifluoromethyl, lower alkoxycarbonyl, lower alkoxycarbonylamino, benzoylamino and/or by di-lower alkylamino.

Lower alkyl $R_5$ and $R_6$ is preferably methyl or n-hexyl.

Alkylthio having up to 20 carbon atoms $R_7$ has preferably from 10 to 18, especially from 10 to 14, carbon atoms and is such a branched or especially straight-chain alkylthio, such as especially n-dodecylthio.

Alkanoyloxy having up to 20 carbon atoms $R_7$ is preferably lower alkanoyloxy, for example acetoxy.

4-(2,3,4,6-Tetra-O-acetyl-$\beta$-D-glucopyranos-1-yloxy)-phenoxy $R_7$ is the radical derived from tetra-O-acetyl-arbutin.

Cholestan-3-yloxy $R_7$ is preferably 5$\alpha$-cholestan-3$\beta$D-yloxy.

Aliphatic hydrocarbyl having from 6 to 24 carbon atoms $R_7$ is an aliphatic hydrocarbon radical having from 6 to 24, especially from 6 to 20, carbon atoms, that is to say such an alkynyl or preferably alkyl or alkenyl radical. Such a hydrocarbyl radical preferably has from 12 to 18 carbon atoms. Such an alkyl radical is, for example, straight-chain, such as n-dodecyl, n-tetradecyl, n-octadecyl or especially n-hexadecyl, or branched, such as 1,1,2-trimethyl-propyl (texyl). Such an alkenyl radical has preferably 18 carbon atoms and is, for example, cis- or trans-9-octadecenyl, -9,12-octadecadienyl or -9,11,13-octadecatrienyl.

Unsubstituted or substituted phenyl $R_7$ is preferably unsubstituted phenyl. Substituted phenyl $R_7$ is especially phenyl substituted by from one to preferably not more than three customary phenyl substituents, for example by lower alkyl, lower alkoxy, halogen, trifluoromethyl, lower alkoxycarbonyl, lower alkoxycarbonylamino, benzoylamino and/or by di-lower alkylamino.

Aliphatic hydrocarbyloxy having up to 24 carbon atoms $R_7$ is hydrocarbyl bonded via oxygen and containing up to 24, preferably up to 18, carbon atoms, that is to say such an alkynyloxy or preferably alkoxy or alkenyloxy radical. Such a hydrocarbyloxy radical preferably has from 1 to 3 or from 12 to 18 carbon atoms. Such an alkoxy radical is, for example, straight-chain, such as n-dodecyloxy, n-tetradecyloxy, n-octadecyloxy or especially n-hexadecyloxy. A preferred alkoxy radical is also methoxy. Such an alkenyloxy radical has preferably 18 carbon atoms and is, for example, trans- or cis-9-octadecenyloxy, -9,12-octadecadienyloxy or -9,11,13-octadecatrienyloxy, preferably cis-9-octadecenyloxy. Cholesteryloxy- or cholestan-3-yloxy-substituted aliphatic hydrocarbyloxy $R_7$ is preferably aliphatic hydrocarbyloxy substituted in the $\omega$-position, that is to say terminally, by cholesteryloxy or cholestan-3-yloxy, such as especially 5$\alpha$-cholestan-3$\beta$-yloxy, such as especially so substituted alkoxy having from 12 to 18 carbon atoms, for example $\omega$-cholesteryloxy-n-hexadecyloxy.

Aliphatic hydrocarbyl having up to 24 carbon atoms $R_8$ is an aliphatic hydrocarbon radical having up to 24 carbon atoms, that is to say such an alkynyl or preferably alkyl or alkenyl radical. Such a hydrocarbyl radical preferably has from 12 to 18 carbon atoms. Such an alkyl radical is, for example, straight-chain, such as n-dodecyl, n-tetradecyl, n-octadecyl or especially n-hexadecyl, or branched, such as 1,1,2-trimethyl-propyl (texyl). Such an alkenyl radical has preferably 18 carbon atoms and is, for example, cis- or trans-9-octadecenyl, -9,12-octadecadienyl or -9,11,13-octadecatrienyl.

Cholesteryloxy-substituted aliphatic hydrocarbyl $R_8$ is preferably aliphatic hydrocarbyl substituted by cholesteryloxy in the $\omega$-position, for example $\omega$-cholesteryloxy-n-hexadecyl.

A bivalent aliphatic hydrocarbon radical X having up to 23 carbon atoms is a radical in which the two free valencies may originate from the same carbon atom or from different, preferably terminal, carbon atoms, for example such an alkynylene or preferably alkylene or alkenylene radical. Such a hydrocarbyl radical preferably has from 11 to 17 carbon atoms. Such an alkylene radical is, for example, straight-chain, such as n-undecylene, n-tridecylene, n-heptadecylene or especially n-pentadecylene. Such an alkenylene radical has preferably 17 carbon atoms and is, for example, cis- or trans-9-heptadecenyl, -9,12-heptadecadienyl or -9,11,13-heptadecatrienyl.

Tri-lower alkylsilyl $R_3$ or $R_4$ is, for example, trimethylsilyl.

Lower alkoxy-substituted alkoxy having up to 20 carbon atoms $R_3$ or $R_4$ is especially lower alkoxy-lower alkoxy, such as especially 2-lower alkoxy-ethoxy, for example 2-methoxy-ethoxy.

Hereinbefore and hereinafter the radicals designated "lower" contain up to and including 7, preferably up to and including 4, carbon atoms.

The compounds of formula I have valuable pharmacological properties. They can be used, for example, in photodynamic chemotherapy. This can be demonstrated, for example, by the following experimental procedure:

The compounds of formula I are administered intravenously or topically to mice or rats having transplantable or chemically induced tumours or to hairless mice having transplantates of human tumours. For example, 7 to 10 days after the transplantation of a Meth-A sarcoma, BALB/c mice are treated with a compound of formula I. In a time period of from 1 to 7 days after the single administration of a compound of formula I, the tumour is selectively irradiated with an "argon-pumped-dye-laser" or titanium-sapphire laser at a wavelength of, for example, 678 nm with a light dose of 50 to 300, for example from 100 to 200, Joule/cm$^2$. (The wavelength required in each case depends upon the specifically selected compound of formula I). In this experimental procedure, compounds of formula I in a dose of approximately from 0.01 to 3 mg/kg, for example from 0.1 to 1.0 mg/kg, bring about the complete disappearance of the tumour (tumour necromatised after 3 to 7 days and mice completely healed after about 21 days). Under these conditions the compounds of formula I do not cause any undesirable light sensitisation of the healthy parts of the animals. During a subsequent observation period of 3 months under these conditions neither general photosensitisation nor renewed tumour growth is observed.

In the context of photodynamic therapy, the compounds of formula I can be also be used in the treatment of certain diseases caused by viruses, such as the Kaposi sarcoma occurring in AIDS, for the purpose of virus inactivation (for example in the case of herpes, AIDS) of stored blood, in the treatment of skin disorders, such as psoriasis or ache vulgaris, and in arteriosclerosis. In addition, they can be used in diagnostics, for example for detecting tumours.

Preference is given to compounds of formula I wherein $R_7$ is cholesteryloxy, unsubstituted or cholesteryloxy-substituted aliphatic hydrocarbyloxy having up to 24 carbon atoms in the aliphatic moiety or, when m is 1 and n is 0, aliphatic hydrocarbyl having from 6 to 24 carbon atoms, or is a radical of formula III above wherein X is a bivalent aliphatic hydrocarbon radical having up to 23 carbon atoms, Y is oxygen or the group —NH—, $R_8$ is cholesteryl, aliphatic hydrocarbyl having up to 24 carbon atoms or unsubstituted or cholesteryloxy-substituted aliphatic hydrocarbyl having up to 24 carbon atoms in the aliphatic moiety, and the other substituents are as defined above.

Special preference is given to compounds of formula I wherein

M is germanium, $R_1$ and $R_2$ each represents the same radical of formula II wherein m is 0 or 1, n is an integer from 0 to 20 inclusive, $R_5$ and $R_6$ are each independently of the other lower alkyl or phenyl and $R_7$ is cholesteryl, cholesteryloxy, alkyl having from 6 to 24 carbon atoms, alkoxy having up to 24 carbon atoms, alkenyloxy having up to 24 carbon atoms or ω-cholesteryloxy-alkoxy having up to 24 carbon atoms in the alkoxy moiety, or each represents the same radical of formula III wherein m is 0 or 1, X is alkylene having up to 23 carbon atoms, Y is oxygen, $R_5$ and $R_6$ are each phenyl or lower alkyl and $R_8$ is cholesteryl, $R_3$ is hydrogen, tri-lower alkylsilyl or unsubstituted or lower alkoxy-substituted alkoxy having up to 20 carbon atoms, and $R_4$ is hydrogen.

Very special preference is given to compounds of formula I wherein

M is germanium, $R_1$ and $R_2$ each represents the same radical of formula II wherein m is 0 or 1, n is an integer from 0 to 5 inclusive, $R_5$ and $R_6$ are each phenyl or lower alkyl and $R_7$ is cholesteryloxy, alkoxy having up to 18 carbon atoms, $C_{18}$alkenyloxy, alkyl having from 6 to 18 carbon atoms, ω-cholesteryloxy-$C_{12-18}$alkoxy, phenyl, cholestan-3-yloxy, 4-(2,3,4,6-tetra-O-acetyl-β-D-glucopyranos-1-yloxy)-phenoxy, $C_{10-14}$alkylthio or lower alkanoyloxy, or wherein $R_1$ and $R_2$ each represents the same radical of formula HI wherein m is 1, X is $C_{11-17}$-alkylene, Y is oxygen, $R_5$ and $R_6$ are each phenyl and $R_8$ is cholesteryl, $R_3$ is hydrogen or lower alkoxy-substituted lower alkoxy, and $R_4$ is hydrogen.

Very particular preference is given to compounds of formula I wherein

M is germanium, $R_1$ and $R_2$ each represents the same radical of formula II wherein m is 0 or 1, n is 0, 2, 3 or 5, $R_5$ and $R_6$ are each phenyl, methyl or n-hexyl and $R_7$ is cholesteryloxy, methoxy, n-hexadecyloxy, cis-9-octadecenyloxy, n-hexyl, 1,1,2-trimethyl-propyl, n-octadecyl, ω-cholesteryloxy-n-hexadecyloxy, phenyl, 5-α-cholestan-3-β-yloxy, 4-(2,3,4,6-tetra-O-acetyl-β-D-glucopyranos-1-yloxy)-phenoxy, n-dodecylthio or acetoxy, or wherein $R_1$ and $R_2$ each represents the same radical of formula III wherein m is 1, X is n-pentadecylene, Y is oxygen, $R_5$ and $R_6$ are each phenyl and $R_8$ is cholesteryl, $R_3$ is hydrogen or 2-methoxy-ethoxy, and $R_4$ is hydrogen.

Most preference is given to the compounds of formula I described in the Examples.

The compounds of formula I are prepared according to processes known per se. The process according to the invention is carried out as follows: a compound of formula V wherein $R_{11}$ is hydroxy or halogen, and $R_{12}$ has the same definition as $R_{11}$ when M is an element of main group IV, or $R_{12}$ is absent when M is an element of main group III or ruthenium, and the other symbols are as defined above, is reacted with a compound of formula VI $R_1$—H   (VI)

wherein $R_1$ is as defined above, or with a reactive derivative thereof having an activated OH group.

Halogen $R_{11}$ is preferably chlorine.

A reactive derivative of a compound of formula VI having an activated OH group is a derivative in which the terminal OH group is in reactive esterified form, for example in the form of an ester with a mineral acid, for example a hydrohalic acid or sulfuric acid, or a sulfonic acid, such as p-toluenesulfonic acid. A preferred reactive derivative is a halide, such as especially a chloride.

Preferably a compound of formula V wherein $R_{11}$ is hydroxy is reacted with a compound of formula VI having a terminal OH group, that is to say with a compound of the formula $R_1$—H. Alternatively, it is also possible to react a compound of formula V wherein $R_{11}$ is hydroxy with a reactive derivative of a compound of formula VI having an activated OH group, for example a halide.

In most cases it is preferable to carry out the reaction in a suitable inert solvent, for example an aromatic hydrocarbon, such as toluene or benzene, an ether, such as especially a cyclic ether, such as preferably dioxane, or a solvent mixture, it also being possible to begin with a suspension of the compound of formula V in the said solvent. The reaction temperature depends inter alia upon whether $R_1$ is hydrogen or halogen and whether or not the compound of formula VI is in activated form. Normally the reaction temperature is from room temperature to approximately the boiling point of the solvent or solvent mixture used, and the reaction may, if desired or necessary, be carried out under pressure and/or in an inert gas atmosphere, for example under argon. For the preparation of compounds of formula I wherein $R_1$ is a radical of formula II wherein m and n are each 0 and $R_7$ is aliphatic hydrocarbyloxy having up to 6, especially from 1 to 3, carbon atoms, the corresponding alcohol of the formula $R_7$—H may be used not only as reagent but at the same time also as solvent.

Some of the starting materials of the formulae V and VI are known or they can be prepared in the same manner as or in analogous manner to that described in the Examples.

The invention relates also to the use of the compounds of formula I, preferably in the form of pharmaceutical compositions, in the therapeutic treatment of the human or animal body, especially in the treatment of tumours responsive to photodynamic chemotherapy. The invention relates especially to a method of treating tumours in warm-blooded animals including humans by photodynamic chemotherapy wherein an amount effective in said chemotherapy of a compound of formula I is administered to a said animal in need of said treatment. The dose of the active ingredient depends inter alia upon the nature of the disease, for example the size of the tumour, the nature and size of the species to be treated, and upon the mode of administration. For example, a daily dose of from 1 mg to 100 mg of a compound of formula I will be administered, preferably intravenously, to a warm-blooded animal having a body weight of about 70 kg.

The invention relates also to pharmaceutical compositions comprising the compounds of the present invention as active ingredients and to processes for the preparation of those compositions. The invention relates especially to pharmaceutical compositions for use in the photodynamic chemotherapy of tumours comprising an amount effective in said chemotherapy of a compound of formula I together with a pharmaceutical carrier.

The pharmaceutical compositions according to the invention are, for example, for parenteral, such as especially intravenous, administration to warm-blooded animals.

Compositions for use in photodynamic chemotherapy are especially preferably those which concentrate in the tumour tissue. Especially suitable for this purpose are liposome formulations, for example analogous to those described in the European Patent Application having the Publication No. 451103. Those formulations comprise, in addition to one part by weight of active ingredient, especially from 25 to 100 parts by weight of 1-n-hexadecanoyl-2-(9-cis-octadecenoyl)-3-sn-phosphatidyl-choline (POPC), from 0 to 75 parts by weight of 1,2-di(9-cis-octadecenoyl)-3-sn-phosphatidyl-S-serine (OOPS) and from 0 to 500 parts by weight of lactose.

The following Examples illustrate the invention described above but do not limit the scope thereof in any way. Temperatures are given in degrees Celsius. The numbering of the carbon atoms of the phthalocyanine ring system used in the following Examples corresponds to that used in formula I.

EXAMPLE 1

1 g (1.62 mmol) of dihydroxygermanium-phthalocyanine (prepared in accordance with Joyner et.al., Inorg. Chem. 1, 236 [1962]) is suspended in 100 ml of dioxane, and 1.89 g (3.24 mmol) of diphenylcholesteryloxysilanol are added thereto. The mixture is boiled under reflux for 48 hours. After 20 hours about 20 ml of dioxane are distilled off. The reaction mixture is allowed to cool and concentrated to dryness by evaporation. 600 ml of hexane are added to the residue and the mixture is stirred for 15 minutes and filtered with suction. The filtration residue is washed thoroughly with hexane and chromatographed on aluminium oxide (Alox B) using hexane/tetrahydrofuran (9:1 and 1:1) and pure tetrahydrofuran in succession as eluants. The product-containing fractions are combined and recrystallised from methylene chloride/hexane, yielding bis(diphenylcholesteryloxysiloxy)germanium-phthalocyanine in the form of blue crystals: m.p. 247°–276°, NMR (CDCl$_3$): $\delta = 9.50$ (m,8H); 8.32 (m,8H); 6.70 (m,4H); 6.28 (m, 8H); 4.90 (m,8H); 4.64 (m,2H); 2.1–0 (several m's, cholesterol-H) ppm, UV: 685 nm ($\epsilon = 269000$ in CH$_2$Cl$_2$).

The dihydroxygermanium-phthalocyanine used as starting material is prepared as follows:

Step 1.1

40 g (0.168 mol) of germanium tetrachloride are added to 100 g (0.78 mol) of phthalodinitrile in 200 ml of quinoline (Fluka puriss.) in a sulfonating flask at room temperature. The reaction mixture is heated slowly to a bath temperature of 220° C. and stirred at that temperature for 9 hours. The mixture is then allowed to cool and the product is filtered off using a suction filter. The residue is washed with dimethylformamide and acetone. The blue crystals are transferred to a Soxhlet and extracted overnight first with dimethylformamide, then for 6.5 hours with xylene and again overnight with acetone. Drying under a high vacuum at 70° C. yields dichlorogermanium-phthalocyanine [R. D. Joyner and M. E. Kenney, J. Am. Chem. Soc. 82, 5790 (1960)]. The substance is virtually insoluble in all solvents.

Step 1.2

500 ml of pyridine and 500 ml of 30% ammonia solution (techn.) are added to 27.8 g of dichlorogermanium-phthalocyanine in a 2 liter autoclave and the mixture is heated at 100° for 12 hours, a pressure of 6 bar being attained. After cooling, the residue is filtered off using a suction filter, five times made into a slurry with water and washed neutral. After further washing with ethanol (twice), acetone and diethyl ether (once each), the resulting powder is dried overnight under a high vacuum at 70°, yielding dihydroxy-germanium-phthalocyanine [R. D. Joyner and M. ( 1960)] in the form of a blue, microcrystalline powder. The substance is virtually insoluble in all solvents.

The reagent, diphenylcholesteryloxysilanol, is prepared as follows:

Step 1.3

Variant a (Mitsunobu conditions; Review article in Synthesis 1981, 1; J. Org. Chem. 56, 670 [1991]):

A solution consisting of 5 g (23.1 mmol) of diphenylsilanol, 4.47 g (11.55 mmol) of cholesterol, 6.12 g (23.1 mmol) of triphenylphosphine and 4.7 ml (23.1 mmol) of azodicarboxylic acid diisopropyl ester in 100 ml of abs. tetrahydrofuran is stirred at 50° C. for 3.5 days. The reaction mixture is extensively concentrated and the residue is chromatographed repeatedly on silica gel using hexane/ethyl acetate (2.5:1) as eluant. Diphenylcholesteryloxysilanol is obtained in the form of colourless crystals; m.p. 146°–150° C., NMR (CDCl$_3$): $\delta = 7.68$ (m,4H); 7.40 (m,8H); 5.25 (m, 1H); 3.78 (m, 1H); 2.6–0.5 (several m's, cholesterol-H) ppm.

Variant b (J. Chem. Soc. Chem. Commun. 1987, 325): At room temperature and in the absence of moisture (argon balloon flask), a solution of 7.97 g of cholesterol and 1.62 ml of pyridine in 150 ml of absolute benzene is added dropwise within a period of 45 minutes to a solution of 4.19 ml (20 mmol) of diphenyldichlorosilane in 100 ml of abs. benzene. After a short time a precipitate of pyridine hydrochloride is formed. When the dropwise addition is complete, the mixture is heated to about 60° and then stirred for a further 4 to 5 hours. When the reaction is complete (monitoring by thin layer chromatography), the contents of the flask are transferred with ethyl acetate to a separating funnel and the organic phase is washed with water and saturated sodium chloride solution. After removal of the solvent, the residue is chromatographed on silica gel (hexane/tetrahydrofuran [2.5:1]), yielding diphenylcholesteryloxysilanol, which is identical to that described in Step 1.1.

EXAMPLE 2

200 mg (0.181 mmol) of bis(diphenylhydroxysiloxy)-germanium-phthalocyanine (prepared in accordance with Joyner et. al., J. Inorg. Nucl. Chem. 24, 299 [1962]) are heated at 165° C. together with 500 mg of cholesterol in a bomb tube for 65 hours under argon. After cooling, the residue is chromatographed on Alox B (eluant: $CH_2Cl_2$/hexane [1:1]) and recrystallised from $CH_2Cl_2$/hexane, yielding bis(diphenylcholesteryloxysiloxy)-germanium-phthalocyanine in the form of blue crystals having properties identical to those of the material obtained in accordance with Example 1.

The starting material is obtained as follows:
Step 2.1

0.5 g (0.809 mmol) of germaniumdihydroxyphthalocyanine and 0.524 g (2.42 mmol) of diphenylsilanediol in 10 ml of benzene are boiled under reflux for 4 hours. After cooling, the reaction solution is filtered using a frit and the residue (i.e. unreacted germaniumdihydroxy-phthalocyanine ) is washed with diethyl ether. After removal of the solvent the residue of the filtrate is dissolved in $CH_2Cl_2/CHCl_3$/dioxane and the solvent mixture is concentrated to about 20 ml under normal pressure. On being left to stand at room temperature, bis(diphenylhydroxysiloxy)germanium-phthalocyanine crystallises out in dioxane complex form (Joyner et. al., J. Inorg. Nucl. Chem. 24, 299 [1962]); NMR($CDCl_3$): δ=inter alia 9.50 (m,8H); 8.36 (m,8H); 6.69 (m,4H); 6.33 (m,8H); 5.04 (m,8H) ppm.

EXAMPLE 3

Variant a 1.16 g (1.875 mmol) of germaniumdihydroxyphthalocyanine and 1.65 g of the crude product from Step 3.1, containing diphenylhexadecyloxysilanol, are boiled under reflux in 100 ml of dioxane for 18 hours. The solution is allowed to cool and filtered using a frit. The residue on the frit, which is unreacted starting material, .amounts to 662 mg after drying under a high vacuum. The filtrate is concentrated to an oily residue and dried under a high vacuum, a portion of the substance crystallising out. On the addition of pentane, a very fine, microcrystalline precipitate of the desired product is formed. The precipitate is filtered off, washed with methanol and dried. Recrystallisation of a sample from hot tert-butanol yields crystals of bis(diphenylhexadecyloxy-siloxy)germanium-phthalocyanine; m.p. 87°–89°, NMR ($CDCl_3$): δ=9.62 (m,8H); 8.35 (m,8H); 6.68 (m,4H); 6.31 (m,8H); 4.96 (m,8H); 1.5–0 (remaining H's, of the hexadecyl side chain) ppm.

The starting material for Variant a is obtained as follows:
Step 3.1

1 ml (1.22 g; 4.8 mmol) of diphenylchlorosilane and 4.8 g of poly-Hünig base (diisopropylaminomethylpolystyrene) are placed in 20 ml of toluene. At room temperature, 1.167 g (4.8 mmol) of hexadecanol dissolved in 25 ml of toluene are added slowly dropwise over a period of 50 minutes. The reaction mixture is stirred for 4¼ hours at room temperature. The polymeric base is then removed by filtration with suction and the filtrate is transferred to a separating funnel and diluted with ethyl acetate, and the organic phase is washed twice each with saturated sodium hydrogen carbonate solution and brine. After drying over $Na_2SO_4$ and concentration of the solvent there remains an oily, partially solid residue which is digested with hexane. The solution is filtered with suction, concentrated and dried overnight under a high vacuum. The crude product contains inter alia the desired compound diphenylhexadecyloxysilanol and is used in Example 3, Variant a, without purification.

Variant b 2 g (3.24 mmol) of dihydroxygermanium-phthalocyanine are boiled at reflux with 2 equivalents of diphenylhexadecyloxysilanol in 210 ml of dioxane for 39 hours. After 24 hours, 500 mg of dihydroxygermaniumphthalocyanine are added. The reaction mixture is allowed to cool and the residue is chromatographed on basic aluminium oxide (Alox B) using pure hexane and hexane/ethyl acetate (4:1) in succession as eluants. The product-containing fractions are combined and concentrated. The residue is recrystallised from pentane at −20° C., yielding blue crystals of bis(diphenylhexadecyloxy-siloxy)germanium-phthalocyanine.

The reagent diphenylhexadecyloxysilanol for Variant b is prepared under Mitsunobu conditions analogously to Step 1.3, Variant a; NMR ($CDCl_3$): 7.8–7.0 (2 m's,10H); 3.83 (t,2H); 1.8–0.7 (various m's, hexadecyl-H) ppm.

EXAMPLE 4

Analogously to Example 1, bis(diphenyl-cis-9-octadecenyloxy-siloxy)germanium-phthalocyanine is obtained from 2.99 g (6.4 mmol) of diphenyl-cis-9-octadecenyloxysilanol and 2 g (3.2 mmol) of dihydroxygermanium-phthalocyanine; $UV_{max}$: 674 nm in methanol.

The starting material is obtained as follows:
Step 4.1

Diphenyl-cis-9-octadecenyloxysilanol is prepared under Mitsunobu conditions from 2 g (9.25 mmol) of diphenylsilanediol, 2.08 ml (4.62 mmol) of cis-9-octadecen-1-ol, 2.45 g (9.25 mmol) of triphenylphosphine and 1.88 ml (9.25 mmol) of azodicarboxylic acid diisopropyl ester in 40 ml of tetrahydrofuran analogously to Step 1.3, Variant a.

EXAMPLE 5

Analogously to Example 1, bis(diphenyl-octadecyloxy-siloxy)germanium-phthalocyanine is prepared from 110 mg (0.235 mmol) of diphenyl-octadecyloxysilanol and 73 mg (0.117 mmol) of dihydroxygermanium-phthalocyanine. Diphenyl-octadecyloxysilanol is prepared under Mitsunobu conditions from 2 g (9.25 mmol) of diphenylsilanediol, 2.5 g (9.25 mmol) of 1-octadecanol, 2.99 g (11.1 mmol) of triphenylphosphine and 1.93 ml (11.1 mmol) of azodicarboxylic acid diethyl ester in 40 ml of benzene analogously to Step 1.3., Variant a.

EXAMPLE 6

In analogy to a procedure by Wheeler et.al., J. Am. Chem. Soc. 106, 7404 (1984)] 3.3 g (9.5 mmol)of dimethyl-octadecyl-chlorosilane and 0.5 g (0.8 mmol) of dihydroxygermanium-phthalocyanine in 50 ml of pyridine are stirred for 2 hours at 50°. The solution is cooled and filtered using a suction filter. The solvent is removed in vacuo, and 250 ml of hexane are added to the residue. The resulting precipitate is filtered off with suction and washed fast with hexane, then in portions with 200 ml of acetone/water (1:1). The residue is dried overnight under a high vacuum, then extracted with toluene in a Soxhlet, freed of solvent and dried, yielding bis(dimethyl-octadecyl-siloxy)germanium-phthalocyanine; NMR (pyridine-d5): $\delta=9.8-9.9$ (m, 8H); 8.3–8.5 (m,8H): aromatic H's; 0.75–1.46 (various m's); 0.45(m); −0.03 (m); −0.88 (m); −1.91 (m); −2.48 (m, 4×CH$_3$: silyl side chains) ppm.

Alternatively, bis(dimethyl-octadecyl-siloxy)germanium-phthalocyanine can be prepared by boiling in dioxane dihydroxygermanium-phthalocyanine and dimethyl-octadecylsilanol (described in Helv. Chim. Acta 59, 717 [1976]).

EXAMPLE 7

Analogously to Example 1, bis[(5-cholesteryloxy-3-oxa-pentyloxy)-diphenylsiloxy]germanium-phthalocyanine is obtained from 0.755 g (1.22 mmol) of dihydroxygermanium-phthalocyanine and 1.646 g (2.44 mmol) of 5-cholesteryloxy-3-oxa-pentyloxy)-diphenyl-silanol in 80 ml of dioxane. The silanol is prepared under Mitsunobu conditions analogously to Step 1.3., Variant a, from 1 g (2.1 mmol) of 5-cholesteryloxy-3-oxa-pentan-1-ol, 0.45 g (2.1 mmol) of diphenylsilanediol, 0.661 g (2.52 mmol) of triphenylphosphine and 0.439 ml (2.52 mmol) of azodicarboxylic acid diethyl ester.

Alternatively, 5-cholesteryloxy-3-oxa-pentyloxy)-diphenyl-silanol can also be prepared in accordance with Step 1.3, Variant b, from 0.44 1 ml (2.1 mmol) of diphenylchlorosilane, 0.184 ml (1.1 equiv.) of pyridine and 1 g (2.1 mmol) of 5-cholesteryloxy-3-oxa-pentan-1-ol in 50 ml of THF.

The starting compound for the silanol, 5-cholesteryloxy-3-oxa-pentan-1-ol, is obtained as follows (see Bull. Soc. Chim. France 1960, 297; J. Chem. Soc. 1962, 178):

Step 7.1

50 g (0.129 mmol) of cholesterol are dissolved in 250 ml of pyridine and cooled to about 5° C. with ice/water. Under argon, 49 g (0.258 mol) of tosyl chloride are added in portions thereto. When the addition is complete, the mixture is stirred for a further 15 minutes with cooling. The ice-bath is then removed and the mixture is stirred for 2 days at room temperature to complete the reaction. The resulting fine suspension is poured onto 1.2 liters of ice-water and stirred for 30 minutes. The precipitate is filtered off with suction, washed thoroughly with H$_2$O and dried under a high vacuum at 40°. The substance, which still contains a large amount of pyridine hydrochloride, is dissolved in CH$_2$Cl$_2$ and the organic phase is washed twice with water, once with 1N hydrochloric acid and again with water. After drying over Na$_2$SO$_4$ and concentration in a rotary evaporator, the residue is recrystallised from CH$_2$Cl$_2$/hexane, yielding cholesteryl tosylate; m.p. 130°–131°.

Step 7.2

20 g (36.98 mmol) of cholesteryl tosylate and 133 ml (44.38 mmol) of diethylene glycol in 275 ml of dioxane (Fluka puriss.) are boiled under reflux for 2¾ hours. The cooled solution is extensively concentrated, the residue is taken up in water and extracted three times with diethyl ether. The organic phase is washed twice with water and once with brine. After drying over Na$_2$SO$_4$ and removal of the solvent, the residue is chromatographed on silica gel with hexane/ethyl acetate (2.5:1), yielding 5-cholesteryloxy-3-oxa-pentan-1-ol in the form of a waxy product.

EXAMPLE 8

Analogously to Example 1, bis[diphenyl-(3,6,9,12,15-pentaoxa-hexadec-1-yloxy)-siloxy]germanium-phthalocyanine is obtained from 40 mg (0.064 mmol) of dihydroxygermanium-phthalocyanine and 50 mg (0.132 mmol) of diphenyl-(3,6,9,12,15-pentaoxa-hexadec-1-yloxy)-silanol in 8 ml of dioxane; UV$_{max}$=676 nm (CH$_2$Cl$_2$).

The starting material is obtained as follows:

Step 8.1

19.02 g (0.116 mol) of triethylene glycol monomethyl ether and 21 ml (20.54 g=0.26 mol) of pyridine in 110 ml of benzene are heated to reflux, and 19 ml (31 g=0.26 mol) of thionyl chloride are added dropwise thereto. The mixture is boiled under reflux for a further 20 hours. When the reaction solution has cooled, a mixture consisting of 5 ml of concentrated hydrochloric acid and 20 ml of water is added thereto, with stirring. The organic phase is separated off and washed repeatedly with water and brine. The solvent is extensively distilled off using a Vigreux column and the residue is purified on silica gel in hexane/ethyl acetate (4:1). The product-containing fractions are concentrated and the residue is distilled, yielding 3,6,9-trioxadecyl chloride (J. Am. Chem. Soc. 89, 7017 (1967)); b.p. 76° C./2 mbar, NMR (CDCl$_3$): 3.8–3.5 (m,12H); 3.37 (s,3H)

Step 8.2

Under argon, 630 mg (27.4 mmol) of sodium are added to 10 ml of diethylene glycol and the mixture is heated for one hour at 100° C. At that temperature, 5 g (27.4 mmol) of 3,6,9-trioxadecyl chloride are added dropwise thereto using a syringe. The mixture is stirred overnight at 100° C. to complete the reaction. After cooling, the reaction solution is taken up in CH$_2$Cl$_2$, washed with water and brine and dried over Na$_2$SO$_4$. Removal of the solvent yields 3,6,9,12,15-pentaoxa-hexadecanol in the form of an oil (Liebigs Ann. Chem. 1980, 858); NMR(CDCl$_3$): 3.8–3.5 (m,20H); 3.75 (s,3H).

Step 8.3

Under Mitsunobu conditions, diphenyl-(3,6,9,12,15-pentaoxa-hexadec-1-yl-oxy)-silanol is obtained analogously to Step 1.3., Variant a, from 2 g (7.83 mmol) of 3,6,9,12,15-pentaoxa-hexadecanol, 3.39 g (21.63 mmol) of diphenylsilanediol, 4.11 g (15.66 mmol) of triphenylphosphine and 3.2 ml (3.17 g; 15.7 mmol) of azodicarboxylic acid diisopropyl ester in 70 ml of tetrahydrofuran; NMR(CDCl$_3$): 7.1–7.8 (m's, phenyl-H); 3.4–3.7 (m,OCH$_2$—CH$_2$); 3.35 (s,3H,OCH$_3$).

Alternatively, the same compound can also be obtained in accordance with Step 3.1. from diphenylchlorosilane and 3,6,9,12,15-pentaoxa-hexadecanol in the presence of pyridine.

EXAMPLE 9

Analogously to Example 1, bis[diphenyl-(ω-cholesteryloxycarbonyl-n-pentadec-1-yloxy)-siloxy]germanium-phthalocyanine is obtained from dihydroxygermanium-phthalocyanine and diphenyl-(m-cholesteryloxycarbonyl-n-pentadec-1-yloxy)-silanol. The silanol used is prepared under Mitsunobu conditions analogously to Step 1a. The preparation of the starting compound for the silanol, cholesteryl-1-hydroxy-palmitate, is effected using the tetrahydropyranyl ether protecting group, with subsequent removal in accordance with analogous procedures from the literature (Lipids 14, 816 [1979]; Synthetic Commun. 16, 1423 [1986]).

EXAMPLE 10

The following compounds are obtained analogously to the processes described in this Application:
di(ω-cholesteryloxy-n-hexadecyloxy)germanium-phthalocyanine,
bis[(ω-cholesteryloxy-n-hexadecyloxy)-diphenyl-siloxy]germanium-phthalocyanine
bis[(8-cholesteryloxy-3,6-dioxa-octyloxy)-diphenyl-siloxy]germanium-phthalocyanine and
di(8-cholesteryloxy-3,6-dioxa-octyloxy)germanium-phthalocyanine.

EXAMPLE 11

A mixture of 242 mg (0.2 mmol) of 1,4,8,11,15,18,22,25-octakis(2-methoxy-ethoxy)dihydroxy-germanium-phthalocyanine, 350 mg (0.6 mmol) of diphenylcholesteryloxysilanol (see Step 1.3), 3 ml of pyridine and 30 ml of abs. toluene is heated at reflux for one hour. The mixture is then evaporated to dryness and the residue is dissolved in diethyl ether and washed four times with water. The solvent is evaporated off and the residue is chromatographed over 60 g of basic aluminium oxide (Alox B) with $CHCl_3$. The green eluates are freed of solvent and the residue is crystallised from diethyl ether, yielding 1,4,8,11,15,18,22,25-octakis(2-methoxy-ethoxy)-bis(diphenylcholesteryloxysiloxy)-germanium-phthalocyanine; m.p. 117°–118°, $\lambda_{max}$ ($CHCl_3$): 750nm.

The starting material is obtained as follows:

Step 11.1

A mixture of 32 g (0.2 mol) of 2,3-dicyano-hydroquinone, 104 g (0.24 mol) of 4-(2-methoxy-ethyl)-toluenesulfonate, 126 g of $K_2CO_3$ and 600 ml of dimethylformamide is stirred under nitrogen for 2 hours at 85°. The mixture is then evaporated to dryness in vacuo, and 400 ml of ice-water and 400 ml of $CHCl_3$ are added to the residue and the mixture is filtered. The filtration residue is washed thoroughly with $CHCl_3$. The filtration residue is dried, yielding 3,6-bis(2-methoxy-ethoxy)phthalodinitrile (analogous to J. Chem. Soc. Perk. Trans. 1988, 2453–58); m.p. 152°–154°.

Step 11.2

4.4 g (0.016 mol) of 3,6-bis(2-methoxy-ethoxy)phthalodinitrile (analogous to J. Chem. Soc. Perk. Trans. 1988, 2453–58) are added to a solution of 1.1 g (0.16 mol) of lithium in 120 ml of ethylene glycol monomethyl ether and heated at reflux for 2.5 hours. When the reaction mixture has cooled, 80 ml of acetic acid are added dropwise thereto with ice-cooling. The mixture is stirred for one hour at room temperature, evaporated to dryness in vacuo and the residue is dissolved in methylene chloride and washed with 1N hydrochloric acid and sodium chloride solution. After the solvent has been evaporated off, the residue is chromatographed twice over aluminium oxide, the first time in tetrahydrofuran/chloroform (1:1) and the second time in tetrahydrofuran, yielding 1,4,8,11,15,18,22,25-octakis(2-methoxy-ethoxy)phthalocyanine; m.p. 156°, UV-$_{max}$=760 nm ($CHCl_3$).

Step 11.3

A mixture of 1.1 g (1 mmol) of 1,4,8,11,15,18,22,25-octakis(2-methoxy-ethoxy)phthalocyanine, 3.7 g (10 mmol) of tetrachlorogermanium-dimethylformamide complex (prepared from 7.3 g (0.1 mol) of dimethylformamide, 2.1 g (0.01 mol) of germanium tetrachloride in 50 ml of diethyl ether) and 60 ml of dimethylformamide is boiled at reflux, with stirring, for 22 hours under a nitrogen atmosphere. After cooling and being left to stand at room temperature for 24 hours, 1,4,8,11,15,18,22,25-octakis-(2-methoxy-ethoxy)dichlorogermanium-phthalocyanine is obtained in the form of black crystals having a metallic sheen; m.p. 272° C., $UV_{max}$=781 nm ($CHCl_3$).

Step 11.4

1.6 g (1.3 mmol) of 1,4,8,11,15,18,22,25-octakis(2-methoxy-ethoxy)dichloro-germanium-phthalocyanine are shaken with 150 ml of chloroform and 100 ml of 1N NaOH for 3 minutes at room temperature. The aqueous phase is then washed once with 50 ml of saturated NaCl solution. After the solvent has been evaporated off, 1,4,8,11,15,18,22,25-octakis(2-methoxy-ethoxy)dihydroxy-germanium-phthalocyanine having a melting point of 214°–216° is obtained; $\lambda_{max}$ ($CHCl_3$): 762 nm.

EXAMPLE 12

A mixture of 121 mg (0.1 mmol) of 1,4,8,11,15,18,22,25-octakis(2-methoxy-ethoxy)dihydroxy-germanium-phthalocyanine (see Step 11.4), 319 mg (1 mmol) of chlorotrihexylsilane, 500 mg of triethylamine and 20 ml of β-picoline is heated at reflux for 4 hours. The mixture is then evaporated to dryness in vacuo and the residue is dissolved in diethyl ether and washed five times with saturated NaCl solution. After drying over sodium sulfate and evaporation of the solvent, the residue is dried for 12 hours at 80° under a high vacuum. In this manner there is obtained 1,4,8,11,15,18,22,25-octakis-(2-methoxy-ethoxy)-bis(tri-n-hexyl-silyloxy)germanium-phthalocyanine; $\lambda_{max}$ ($CHCl_3$): 756 nm.

EXAMPLE 13

Analogously to Example 12, 1,4,8,11,15,18,22,25-octakis(2-methoxy-ethoxy)-bis(texyldimethylsiloxy)-germanium-phthalocyanine is obtained from 1,4,8,11,15,18,22,25-octakis(2-methoxy-ethoxy)dihydroxy-germanium-phthalocyanine (see Step 11.4) and texyldimethylchlorosilane; $\lambda_{max}$ ($CHCl_3$): 750 nm.

EXAMPLE 14

A mixture of 121 mg (0.1 mmol) of 1,4,8,11,15,18,22,25-octakis(2-methoxy-ethoxy)dihydroxy-germanium-phthalocyanine (see Step 11.4), 2 mmol of triphenylsilanol, 3 ml of pyridine and 25 ml of abs. toluene is heated at reflux for one hour. The mixture is then evaporated to dryness in vacuo and the residue is dissolved in diethyl ether and washed four times with water. The solvent is evaporated off, yielding 1,4,8,11,15,18,22,25-octakis(2-methoxy-ethoxy)-bis(-triphenylsiloxy)germanium-phthalocyanine; m.p. 149°–151°, $\lambda_{max}$ ($CHCl_3$): 759 nm.

EXAMPLE 15

2.5 g of the crude product from Step 15.1 and 1.32 g of dihydroxygermanium-phthalocyanine are heated at reflux in 100 ml of dioxane for 50 hours. The cooled solution is filtered with suction and the filtrate is concentrated to dryness by evaporation, and hexane is added to the residue. The desired germanium compound is precipitated in the form of a microcrystalline powder which is filtered off with suction, washed thoroughly with hexane and dried. For further purification, the compound is recrystallised from $CH_2Cl_2$/hexane, yielding bis(diphenyl-[5α-cholestan-3β-yloxy]-siloxy)-germanium-phthalocyanine; m.p. 279°–280°, UV=678 nm ($CH_2Cl_2$); NMR ($CDCl_3$): δ=inter alia 9.54 (m) and 8.34 (m; each 8H, phthalocyanine); 6.7 (m), 6.28 (m) and 4.9 (m; total 20H, phenyl).

Step 15.1

A solution of 2 g (4.9 mmol) of 5α-cholestan-3β-ol in 25 ml of toluene is added dropwise at room temperature over a period of 1 hour to a solution of 1 ml (4.9 mmol) of diphenylchlorosilane and 4.9 g of diisopropylaminomethylpolystyrene in 20 ml of toluene. The reaction mixture is stirred for a further 4 hours at room temperature. The precipitate that forms is filtered off and the filtrate is diluted with ethyl acetate, washed twice each with saturated sodium hydrogen carbonate solution and saturated sodium chloride solution and dried over $Na_2SO_4$. The solvent is removed and hexane is added to the residue. The resulting precipitate is filtered off with suction and the filtrate is concentrated by evaporation and dried overnight under a high vacuum. The resulting crude product is processed further without further purification; NMR($CDCl_3$): i.a. m at 7.68, 7.36 and 3.85.

EXAMPLE 16

108 mg (0.175 mmol) of dihydroxygermanium-phthalocyanine and 154 mg (2 equivalents) of tetraacetylarbutin [prepared in accordance with Arch. Pharm. 250, 547 (1912)] are heated under reflux in 25 ml of toluene for 50 hours. The cooled solution is filtered and the filtrate is concentrated to dryness by evaporation and the residue is recrystallised from $CH_2Cl_2$/hexane, yielding bis[4-(2,3,4,6-tetra-O-acetyl-β-D-glucopyranos-1-yloxy)-phenoxy]germanium-phthalocyanine; m.p. 250°–252°, UV=677 nm ($CHCl_3$); NMR($CDCl_3$): δ=inter alia 9.75 (m) and 8.55 (m; each 8H, phthalocyanine); 5.39 (d) and 2.67 (d; each 4H, phenyl); 2.12 (s), 2.08 (2×s) and 1.98 (s, total 24H, OAc).

EXAMPLE 17

A mixture of 121 mg (0.1 mmol) of 1,4,8,11,15,18,22,25-octakis(2-methoxy-ethoxy)dihydroxy-germanium-phthalocyanine, 202 mg( 1 mmol) of n-1-dodecanethiol, 3 ml of pyridine and 25 ml of absolute toluene is heated at reflux for 1 hour. The mixture is then evaporated to dryness in vacuo and the residue is dried under a high vacuum at 75° for 1.5 hours, yielding 1,4,8,11,15,18,22,25-octakis(2-methoxy-ethoxy)-bis(n-1-dodecylthio)germanium-phthalocyanine; $\lambda_{max}$($CHCl_3$): 776 nm.

EXAMPLE 18

Analogously to Example 17, 1,4,8,11,15,18,22,25-octakis(2-methoxy-ethoxy)-bis(n-hexadec-1-yloxy)germanium-phthalocyanine is obtained from 1,4,8,11,15,18,22,25-octakis(2-methoxy-ethoxy)dihydroxy-germanium-phthalocyanine and 1-hexadecanol; $\lambda_{max}$ ($CHCl_3$): 761 nm.

EXAMPLE 19

A mixture of 121 mg (0.1 mmol) of 1,4,8,11,15,18,22,25-octakis(2-methoxy-ethoxy)dihydroxy-germanium-phthalocyanine, 148 mg (1 mmol) of diethylene glycol monoacetate, 3 ml of pyridine and 25 ml of absolute toluene is heated at reflux for 30 minutes. The mixture is then evaporated to dryness, dried at 75° under a high vacuum and crystallised from petroleum ether, yielding 1,4,8,11,15,18,22,25-octakis(2-methoxy-ethoxy)-bis(2-(2-acetoxy-ethoxy)-ethoxy)germanium-phthalocyanine; m.p. 121°–122°, $\lambda_{max}$ ($CHCl_3$): 763 nm.

EXAMPLE 20

200 mg of 1,4,8,11,15,18,22,25-octakis(2-methoxy-ethoxy)dihydroxygermanium-phthalocyanine are boiled in 10 ml of methanol for 2 minutes, filtered and slowly cooled, and the resulting crystals are filtered off, yielding 1,4,8,11,15,18,22,25-octakis(2-methoxy-ethoxy)dimethoxy-germanium-phthalocyanine; m.p. 127°–130°, $\lambda_{max}$ ($CHCl_3$): 761 nm.

EXAMPLE 21

Liposome formulation

In a manner analogous to that described in the European Patent Application having the Publication No. 451103 there is obtained a liposome formulation comprising one part by weight of a compound of formula I, 90 parts by weight of 1-n-hexadecanoyl-2-(9-cis-octadecenoyl)-3-sn-phosphatidyl-choline (POPC), 10 parts by weight of 1,2-di(9-cis-octadecenoyl)-3-sn-phosphatidyl-S-serine (OOPS) and 200 parts by weight of lactose.

EXAMPLE 22

Liposome formulation

In a manner analogous to that described in the European Patent Application having the Publication No. 451103 there is obtained a liposome formulation comprising one part by weight of a compound of formula I, 70 parts by weight of 1-n-hexadecanoyl-2-(9-cis-octadecenoyl)-3-sn-phosphatidyl-choline (POPC), 30 parts by weight of 1,2-di(9-cis-octadecenoyl)-3-sn-phosphatidyl-S-serine (OOPS) and 200 parts by weight of lactose.

What is claimed is:

1. A compound of formula I

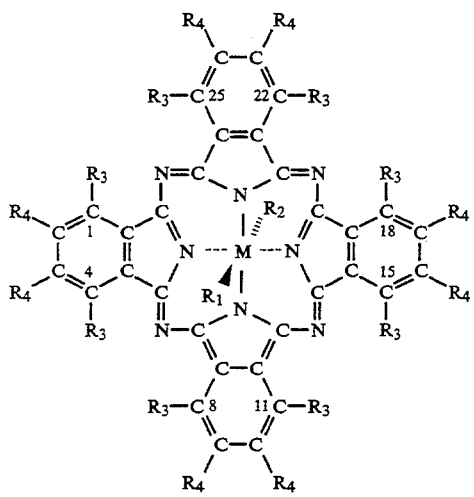

wherein

M is an element of main group III or IV of the Periodic Table having an atomic number of from 31 to 50 inclusive, aluminum or ruthenium, $R_1$ is a radical of formula II

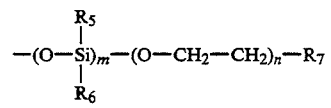

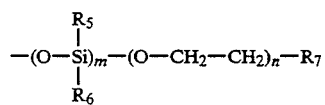

wherein m is 0 or 1, n is an integer from 0 to 200 inclusive, $R_5$ and $R_6$ are each independently of the other lower alkyl or unsubstituted or substituted phenyl, and $R_7$ is cholestan-3-yloxy, cholesteryloxy, unsubstituted or cholestan-3-yloxy- or cholesteryloxy-substituted aliphatic hydrocarbyloxy having from 1 to 24 carbon atoms in the aliphatic moiety, or $R_1$ is a radical of formula III

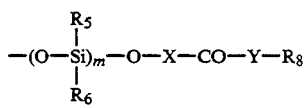

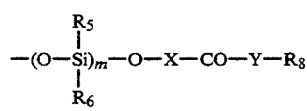

wherein

X is a bivalent aliphatic hydrocarbon radical having from 1 to 23 carbon atoms,

Y is oxygen or the group —NH—, $R_8$ is cholesteryl, or cholesteryloxy-substituted aliphatic hydrocarbyl having from 1 to 24 carbon atoms in the aliphatic moiety, and $R_5$, $R_6$ and m are as defined above, $R_2$ has the same definition as $R_1$ when M is an element of main group W, or $R_2$ is absent when M is an element of main group III or ruthenium, $R_3$ is hydrogen, lower alkyl, lower alkylthio, unsubstituted or lower alkoxy-substituted alkoxy having from 1 to 20 carbon atoms, tri-lower alkylsilyl or halogen, and $R_4$ is hydrogen, lower alkyl, lower alkylthio, unsubstituted or lower alkoxy-substituted alkoxy having from 1 to 20 carbon atoms, tri-lower alkylsilyl or halogen.

2. A compound according to claim 1 of formula I, wherein $R_1$ is a radical of formula II wherein $R_7$ is cholesteryloxy, or cholesteryloxy-substituted aliphatic hydrocarbyloxy having from 1 to 24 carbon atoms in the aliphatic moiety, or $R_1$ is a radical of formula III wherein X is a bivalent aliphatic hydrocarbon radical having from 1 to 23 carbon atoms, Y is oxygen or the group —NH—, and $R_8$ is cholesteryl, or cholesteryloxy-substituted aliphatic hydrocarbyl having from 1 to 24 carbon atoms in the aliphatic moiety.

3. A compound of formula I according to claim 1, wherein

M is germanium, $R_1$ and $R_2$ each represents the same radical of formula II wherein m is 0 or 1, n is an integer from 0 to 20 inclusive, $R_5$ and $R_6$ are each independently of the other lower alkyl or phenyl and $R_7$ is cholesteryl, cholesteryloxy, or ω-cholesteryloxy-alkoxy having from 1 to 24 carbon atoms in the alkoxy moiety, or each represents the same radical of formula III wherein m is 0 or 1, X is alkylene having from 1 to 23 carbon atoms, Y is oxygen, $R_5$ and $R_6$ are each phenyl or lower alkyl and $R_8$ is cholesteryl, $R_3$ is hydrogen, tri-lower alkylsilyl or unsubstituted or lower alkoxy-substituted alkoxy having from 1 to 20 carbon atoms, and $R_4$ is hydrogen.

4. A compound of formula I according to claim 1, wherein

M is germanium, $R_1$ and $R_2$ each represents the same radical of the formula II wherein m is 0 or 1, n is an integer from 0 to 5 inclusive, $R_5$ and $R_6$ are each phenyl or lower alkyl and $R_7$ is cholesteryloxy, ω-cholesteryloxy-$C_{12\text{-}18}$alkoxy, or cholestan-3-yloxy, or wherein $R_1$ and $R_2$ each represents the same radical of formula III wherein m is 1, X is $C_{11\text{-}17}$alkylene, Y is oxygen, $R_5$ and $R_6$ are each phenyl and $R_8$ is cholesteryl, $R_3$ is hydrogen or lower alkoxy-substituted lower alkoxy, and $R_4$ is hydrogen.

5. A compound of formula I according to claim 1, wherein

M is germanium, $R_1$ and $R_2$ each represents the same radical of formula II wherein m is 0 or 1, n is 0, 2, 3 or 5, $R_5$ and $R_6$ are each phenyl, methyl or n-hexyl and $R_7$ is cholesteryloxy, [methoxy, n-hexadecyloxy, cis-9-octadecenyloxy, n-hexyl, 1,1,2-trimethyl-propyl, n-octadecyl,] ω-cholesteryloxy-n-hexadecyloxy, or 5-α-cholestan-3-β-yloxy, [4-(2,3,4,6-tetra-O-acetyl-β-D-glucopyranos-1-yloxy)-phenoxy, n-dodecylthio or acetoxy,] or wherein $R_1$ and $R_2$ each represents the same radical of formula III wherein m is 1, X is n-pentadecylene, Y is oxygen, $R_5$ and $R_6$ are each phenyl and $R_8$ is cholesteryl, $R_3$ is hydrogen or 2-methoxy-ethoxy, and $R_4$ is hydrogen.

6. Bis[diphenyl-($\omega$-cholesteryloxycarbonyl-n-pentadec-1-yloxy)-siloxy]germanium-phthalocyanine according to claim 1.

7. 1,4,8,11,15,18,22,25-Octakis(2-methoxy-ethoxy)-bis(diphenylcholesteryloxysiloxy)germanium-phthalocyanine according to claim 1.

8. Bis(diphenyl-[5$\alpha$-cholestan-3$\beta$-yloxy]-siloxy)germanium-phthalocyanine according to claim 1.

9. A compound according to claim 1, said compound being bis[(5-cholesteryloxy-3-oxa-pentyloxy)-diphenyl-siloxy]germanium-phthalocyanine.

10. The compound of claim 1, said compound being bis(diphenylcholesteryloxysiloxy)germanium-phthalocyanine.

* * * * *

UNITED STATES PATENT AND TRADEMARK OFFICE
CERTIFICATE OF CORRECTION

PATENT NO. : 5,358,940
DATED : October 25, 1994
INVENTOR(S) : Capraro, et. al.

It is certified that error appears in the above-indentified patent and that said Letters Patent is hereby corrected as shown below:

In column 17, line 35, delete formula (II)

In column 17, line 60, delete formula (III)

In column 18, line 3, after "group" delete "w" and insert --IV--in lieu thereof.

In column 18, lines 60-63, after "cholesteryloxy," delete "[methoxy, n-hexadecyloxy, cis-9-octadecenyloxy, n-hexyl, 1,1,2-trimethyl-propyl,n-octadecyl,]"

In column 18, lines 64-66, after "5-α-cholestan-3-β-yloxy, delete "[4-(2,3,4,6-tetra-O-acetyl-β-D-glucopyranos-1-yloxy)-phenoxy, n-dodecylthio or acetoxy,]

Signed and Sealed this

First Day of August, 1995

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,358,940
DATED : October 25, 1994
INVENTOR(S) : Capraro, et al

It is certified that error appears in the above-indentified patent and that said Letters Patent is hereby corrected as shown below:

In column 17, lines 44-45, delete "unsubstituted or"

Signed and Sealed this

Fourth Day of March, 1997

Attest:

BRUCE LEHMAN

*Attesting Officer*  *Commissioner of Patents and Trademarks*